United States Patent (10) Patent No.: US 6,725,074 B1
Kästle (45) Date of Patent: Apr. 20, 2004

(54) QUALITY INDICATOR FOR MEASUREMENT SIGNALS, IN PARTICULAR, FOR MEDICAL MEASUREMENT SIGNALS SUCH AS THOSE USED IN MEASURING OXYGEN SATURATION

(75) Inventor: Siegfried Kästle, Nufringen (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/018,069

(22) PCT Filed: Jun. 10, 1999

(86) PCT No.: PCT/EP99/03994
§ 371 (c)(1),
(2), (4) Date: May 29, 2002

(87) PCT Pub. No.: WO00/77659
PCT Pub. Date: Dec. 21, 2000

(51) Int. Cl.$^7$ .................................................. A61B 5/00
(52) U.S. Cl. ...................................... 600/323; 600/322
(58) Field of Search ................................. 600/322–323, 600/336, 366; 356/39–41

(56) References Cited

U.S. PATENT DOCUMENTS 5,623,929 A * 4/1997 Weng .......................... 600/455

OTHER PUBLICATIONS

Kastle, et al., "A New Family of Sensors for Pulse Oximetry," Hewlett–Packard Journal, Feb. 1997, pp. 39–53.
Morris, et al., "A Comparison of Fifteen Pulse Oximeters. Part I: A Clinical Comparison; Part II: A Test of Performance Under Conditions of Poor Perfusion," Anaesthesia and Intensive Care, Feb. 1989, pp. 62–82.

* cited by examiner

Primary Examiner—Max F. Hindenburg
Assistant Examiner—Matthew Kremer
(74) Attorney, Agent, or Firm—John Vodopia

(57) ABSTRACT

A method of determining a quantitative statement concerning the quality of a medical measurement signal in pulsoximetry includes the steps of determining factors relevant to the measurement signal and interlinking the factors by means of an uncertain logic into a quality indicator. The factors relate to combinations selected from the group consisting of signal recording, signal processing, and signal evaluation. The uncertain logic includes fuzzy logic. The quality indicator quantitatively describes a quality of a determined measurement value of the measurement signal.

12 Claims, 9 Drawing Sheets

Fig. 4A

Figure 1A:
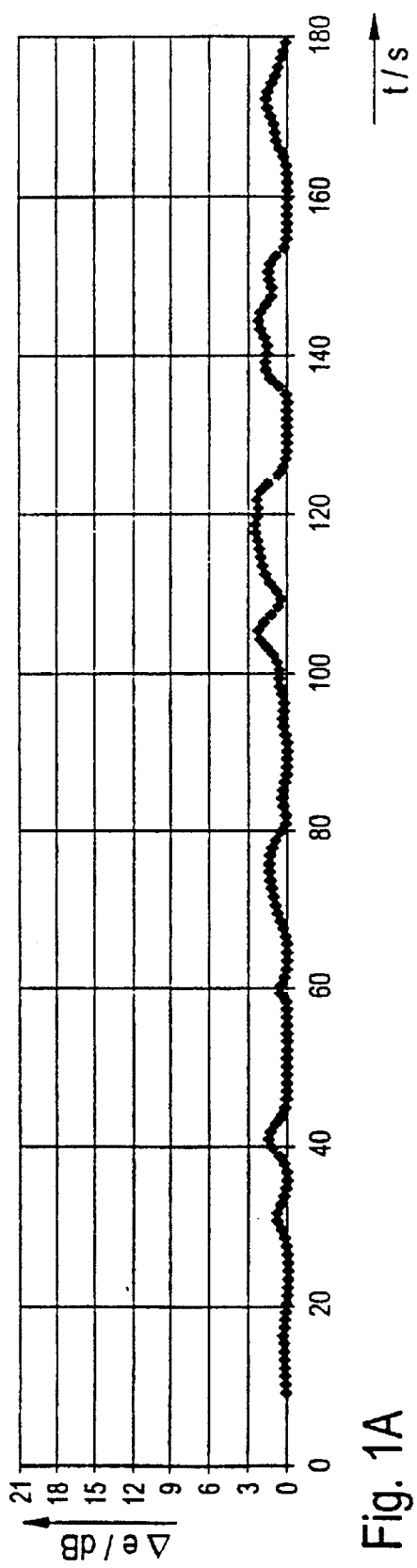

| WENN | | | DANN | |
|---|---|---|---|---|
| Peak Frac | slope FFT | std FFT | DoS | purity FFT |
|  |  | bad | 1.00 | low |
| medium | medium |  | 0.50 | low |
| bad | flat |  | 1.00 | low |
| medium | steep | medium | 1.00 | low |
| perfect | steep | medium | 1.00 | medium |
| medium | medium | medium | 1.00 | medium |
| perfect | medium | medium | 1.00 | medium |
| medium | steep | good | 1.00 | medium |
| medium | medium | good | 1.00 | medium |
| perfect | medium | good | 1.00 | medium |
| perfect | steep | medium | 0.30 | high |
| perfect | steep | good | 1.00 | high |

Fig. 4B

| WENN | | | DANN | |
|---|---|---|---|---|
| correl | energy | spread SpO2 | DoS | purity Signal |
|  | high | high | 1.00 | low |
| low |  |  | 1.00 | low |
|  | low | low | 1.00 | low |
| medium | medium | low | 1.00 | medium |
| medium | medium | low | 1.00 | medium |
| high | medium | medium | 0.40 | medium |
| medium | low | medium | 1.00 | medium |
| high | low | medium | 1.00 | medium |
| medium | medium | medium | 1.00 | medium |
| high | medium | low | 1.00 | medium |
| high | low | low | 1.00 | high |
| high | medium | low | 0.60 | high |

Fig. 4C

| WENN | | | DANN | |
|---|---|---|---|---|
| conti Strength | purity FFT | purity Signal | DoS | inst QI |
| small | low | low | 1.00 | very low |
| medium | low | low | 1.00 | very low |
| small | medium | low | 1.00 | very low |
| medium | medium | low | 1.00 | very low |
| small | high | low | 1.00 | very low |
| small | low | medium | 1.00 | very low |
| small | medium | medium | 1.00 | very low |
| small | low | high | 1.00 | very low |
| very small | | | 1.00 | very low |
| large | low | low | 1.00 | low |
| large | medium | low | 1.00 | low |
| medium | high | low | 1.00 | low |
| medium | low | medium | 1.00 | low |
| large | low | medium | 1.00 | low |
| medium | medium | medium | 1.00 | low |
| small | high | medium | 1.00 | low |
| medium | low | high | 1.00 | low |
| small | medium | high | 1.00 | low |
| small | high | high | 1.00 | low |
| very large | low | low | 1.00 | medium |
| very large | medium | low | 1.00 | medium |
| large | high | low | 1.00 | medium |
| very large | low | medium | 1.00 | medium |
| large | medium | medium | 1.00 | medium |
| medium | high | medium | 1.00 | medium |
| large | low | high | 1.00 | medium |
| medium | medium | high | 1.00 | medium |
| medium | high | high | 1.00 | medium |
| very large | high | low | 1.00 | high |
| very large | medium | medium | 1.00 | high |
| large | high | medium | 1.00 | high |
| very large | low | high | 1.00 | high |
| large | medium | high | 1.00 | high |
| large | high | high | 1.00 | high |
| very large | high | medium | 1.00 | very high |
| very large | medium | high | 1.00 | very high |
| very large | high | high | 1.00 | very high |

QUALITY INDICATOR FOR MEASUREMENT SIGNALS, IN PARTICULAR, FOR MEDICAL MEASUREMENT SIGNALS SUCH AS THOSE USED IN MEASURING OXYGEN SATURATION

BACKGROUND OF THE INVENTION

The invention relates to the determination of a quantitative statement concerning the quality of a measurement signal, preferably a medical measurement signal, such as in pulsoximetry.

Measuring of signals usually comprises a process in several stages, typically with the steps of signal recording, signal processing, and signal evaluation. In the simplest case of a measurement, the mere signal recording suffices, but depending on the application the signal processing and/or evaluation are also regularly necessary.

In signal recording, signals representing the quantity to be measured are recorded as basic signal values, for example by means of a sensor or some other suitable recording device. In some cases, for example in electrocardiography (ECG), these recorded basic signal values already directly represent the measurement quantity to be determined (also called parameter). In other cases, for example the determination of oxygen saturation ($SpO_2$), the recorded basic signals indirectly represent the desired measurement quantity, and a signal evaluation is still necessary in each case so as to derive the desired measurement quantity from the basic signals.

Depending on the measurement process, the measurement accuracy, and influences on the measurement, it is necessary for the basic signals (both those directly and those indirectly representing the measurement quantities) to undergo a signal processing, i.e. the basic signals must be suitably adapted, for example through an improvement in the signal quality such as the signal to noise ratio, or through filtering or suppression of undesirable measurement influences.

Similarly, a signal evaluation is also necessary, depending on the measurement process and the measurement quantity, so as to obtain from the recorded basic signals or the processed signals the desired measurement value of the measurement quantity. As was noted above, the quantities representing the measurement quantity indirectly only are to be evaluated, because the obtained basic signals by themselves are not conclusive.

Given the fact that the obtained measurement values represent the result of the measurement process, or that further quantities, conclusions, or consequences are derived from these measurement values, the question often arises in how far the obtained measurement values can be relied on, i.e. how well or how badly these measurement values represent the actual values of the quantity measured. The reliability or quality of the measurement values is of major importance in particular in the field of medical applications, such as patient monitoring, because a measurement value incorrectly representing the quantity to be measured, while this incorrectness is not observable, may have serious consequences for a patient's life and health, for example owing to an incorrectly prescribed or omitted therapy, or owing to a suppressed alarm function.

A good example of the importance of the quality of measurement values is found in pulsoximetry, where this has frequently led to problems in the past, while at the same time the requirements were set higher and higher. Pulsoximetry is a non-invasive, continuous determination of the oxygen content of the blood (oximetry) based on an analysis of the photospectrometrically measured pulse. It is necessary in this field that a pulse curve (plethysmogram) should be available at several wavelengths. Practically all appliances operate at only two wavelengths, which renders possible inexpensive, compact solutions. The principle of photometry is based on the fact that the quantity of absorbed light is determined by the degree of absorption of a substance and by the wavelength. Pulsoximeters utilize this in that the arterial blood volume, and only the arterial blood volume, pulsates in the rhythm of the heartbeat. The basic principle and the application possibilities of pulsoximetry are generally known and have frequently been described, in particular in EP-A-262778 (with a good summary of the theory), U.S. Pat. No. 4,167,331, or Kästle et al. in "A New Family of Sensors for Pulsoximetry", Hewlett-Packard Journal, vol. 48, no. 1, pp. 39–53, February 1997.

Although ever more difficult cases, as regards the signal quality of the pulsoximetric measurement, are still used for deriving measurement values, there has until now not been a conclusive indicator for the clinical user which renders it possible to evaluate conclusively the reliability and quality of the measurement values obtained. Such an evaluation, however, is important because the pulsoximeters with their plethysmographic basic signals contain too little information for deciding with full certainty in boundary cases whether a measurement value can be indicated. A doctor, for example, regularly has substantially more information available to him for deciding whether the oxygen supply of his patient is actually critical or whether there is merely an artifact of the pulsoximeter.

The aids frequently available to the user of the pulsoximetrical measurement are a representation of the basic signal in the form of a curve (plethysmogram) or the one-dimensional representation as a pulsating histogram bar. In addition, there are warning signals such as "motion", "noise", "low signal" in text fields on displays, or flashing displays (cf. Maurice et al., A Comparison of Fifteen Pulsoximeters, Anesth. Intens. Care, vol. 17, pp. 62–82, 1989).

A first step towards achieving a quality indicator for the pulsoximetrical measurement values can be found in EP-A-587009. A bar display is described therein which is controlled by the transmission (light transmission of the tissue), i.e. by the absolute signal strength (DC component) of the measurement signal. This system, indeed, is certainly capable of indicating an unsuitable measuring location, for example because the received luminous intensity is too low. Nevertheless, the AC component (perfusion) and the interference level remain unconsidered, so that an indication with a high rating for the quality level does not give any guarantee for a reliable measurement.

The user may indeed get a certain indication as to the quality of the signal through judging the size and shape of the plethysmogram and the other displayed quantities. The conclusiveness thereof, however, is limited. A problem is, for example, that only one basic signal is often displayed as the plethysmogram, while the pulsoximeter evaluates two basic curves.

The N-400 Fetal Oxygen Saturation Monitor from the Nellcor Puritan Benett Company has at its front a triangular rod display serving as a multi-parameter reliability indicator for the average signal quality. This signal quality indicator represents the quality of the signal which is used for calculating the $SpO_2$ value. When the signal quality drops to below a required threshold value, an acoustic alarm signal is triggered upon the loss of the signal.

A further method of testing the obtained pulsoximetric measurement value is described in EP-A-904727 and is based on a comparison of the pulse frequency of the pulsoximeter with the heartbeat frequency of the ECG signal. If, for example, the deviation between the two lies within a range of only a few beats per minute, the pulsoximeter is considered credible. If this difference is greater, however, the pulsoximeter readings are considered doubtful.

It is a disadvantage in most of the methods of determining the credibility of the pulsoximetrical measurement value mentioned above that at most only half of the measurement signals available is actually used. Thus, for example, only one of the basic signals suffices for deriving the pulse rate, so that the function of the other channel usually remains fully untested. Alternatively, the periodicity of the signal only is evaluated, while, for example, the amplitude of the basic curve remains substantially unconsidered. This results in numerous potential errors, which are often not even noticeable. If erroneous measurement values or erroneous quality indicators for the measurement values lead to, for example, alarm functions being triggered, and such an erroneous triggering of the alarm is recognizable to the clinical personnel, said alarm functions are often switched off in the clinical operation so as to avoid unnecessary alarms. This, however, may lead to the possibly fatal consequence that the switching-off also means that actual alarm situations are not recognized or are recognized too late. Conversely, an error which is not recognized or heeded may have the result that the obtained measurement value is trusted, although it deviates from the actual value. Life-threatening situations may thus remain unrecognized owing to the reliance placed on the correctness of the measurement value.

SUMMARY OF THE INVENTION

It is accordingly an object of the present invention to provide an improved statement on the reliability of obtained measurement values, in particular in medical applications such as pulsoximetry. The object is achieved by means of the characteristics of the independent claims. Advantageous embodiments are defined in the dependent claims.

According to the invention, the determination of a quantitative statement concerning the quality of a measurement signal, preferably a medical measurement signal such as in pulsoximetry, takes place through the determination of factors which preferably relate to signal recording, signal processing, and/or signal evaluation. A link is established between these determined factors by combinatory processes, in particular by an uncertain logic such as, for example, fuzzy logic, so as to obtain a quality indicator which quantitatively describes the quality of the determined measurement value.

Available examples of factors relevant to signal recording are factors which describe the measurement location, the measurement time, the measurement sensor system, or the like.

Factors relevant to signal processing may be, for example, the signal-to-noise ratio, parameters of a possible subsequent noise suppression, or signal compression, or the like.

Factors relevant to signal evaluation may be determined in particular by the measurement algorithm(s) used, consideration of all basic signals or only part thereof.

It is obvious that the inclusion of as many as possible of such relevant factors, depending on the application, renders it possible to improve the "quality" of the quality indicator. It is alternatively possible, however, to restrict the links to only a few selected factors, in dependence on the application or subject to, for example, computer limitations.

The quality indicator is preferably visually represented by a suitable display, for example between a minimum value and a maximum value. The maximum value is shown in the case of an ideal signal, indicating the highest degree of reliability. As the noise component increases, the quality indicator will drop down to the lower limit of the minimum value, indicating the lowest degree of reliability. In that case the signal is so weak or so strongly noise-laden that it is highly probable that the derived measurement values have major errors and should accordingly not be displayed anymore, or only with a suitable warning.

The level of the quality indicator thus provides a relative measure as to the reliability which the measurement values may be presumed to have. It is clear, however, that an exact prognosis of reading errors cannot be guaranteed, especially not in each and every individual case. Lower values of the quality indicator (low reliability), however, do make the user aware that the readings may be doubtful. The user may then test them by alternative means or may try to achieve a better signal quality, and thus a more reliable measurement, for example through the choice of an alternative measurement location or the use of a different sensor. The quality indicator according to the invention supplies the relevant clues for this.

The relevant factors are preferably linked through the use of known principles of fuzzy logic as described in particular in Altrock C. "Fuzzy Logic: Band 1. Technologie" (Fuzzy Logic: Part 1. Technology), Oldenburg Verlag, Munich, 1995, so that these principles need not be discussed here in any detail and a reference to this and other background literature suffices. Reference is also made to the standard work on statistics by Kreyszig E. "Statistische Methoden und ihre Verwendung" (Statistical Methods and Their Use), Vandenhoek & Ruprecht, Göttingen, 1975, with regard to statistical criteria and algorithms.

In a preferred embodiment, the quality indicator according to the invention is presented in the form of a tendency indication in the sense of "relatively better/worse" or "absolutely good/bad", for example by means of a quasi-analog display with histogram bars of variable length. This renders possible a satisfactory and sufficiently intuitively recognizable representation of the quality indicator according to the invention.

In another preferred embodiment, a further visualization of the quality indicator according to the invention takes place such that the display method for the measurement quantity described by the quality indicator changes when the quality indicator value exceeds one or several given threshold values. This may take place, for example, through a switch-over from a continuous display to a flashing display (possibly with a varying flashing frequency in dependence on the quality indicator value), through a change in the display color (for example, red in the case of low quality indicator values or as in a traffic light: green for a high, amber for an average, and red for a low quality indicator value), or by an inversion of the colors. This not only gives an intuitively recognizable impression of the display value of the quality indicator but also a reliable call to attention in the case of any critical measurement situations.

In a further preferred embodiment of the invention, an alarm function is controlled (for example upon a deviation of the measurement signal from a given value or range) in dependence on the quality indicator. Preferably, such a control takes place through a change in an alarm delay period (i.e. the time between the moment an alarm-triggering criterion is reached and the actual triggering of the alarm) in dependence on the value of the quality indicator. Since the quality indicator is a measure for the signal quality, the alarm delay time is preferably set for a maximum in the case of a bad signal and an accompanying low quality indicator value (=low reliability), because the probability of a false alarm is very high here. At high values of the quality indicator (=high reliability), the risk of a false alarm is small, and the alarm delay time may be reduced, which in its turn provides a chance of a fast recognizability in the case of actual alarm situations.

In a further embodiment, an evaluation of the gradient in time of the quality indicator takes place so as to be able to recognize trends and to derive therefrom, for example, error prognoses. Preferably, such a trend is displayed in addition to the display of the quality indicator value, for example through a display of an arrow pointing upwards for an improvement of the signal quality, an arrow pointing downwards for a deterioration of the signal quality, and an arrow remaining at the same level for indicating a signal quality which remains substantially the same. Furthermore, an error prognosis is possible by means of the gradient of the quality indicator trend, so that an alarm signal can be given, for example in the case of a continuous downward trend of the quality indicator value over a given period, also if the absolute value of the quality indicator should still be within an acceptable range.

The values of the determined quality indicator and/or the trend of the quality indicator are preferably recorded at the same time so that they can be taken into account in a subsequent evaluation of the measurement. This renders it possible, for example, to qualify measured occurrences as artifacts or as genuine occurrences later.

The invention is used preferably for medical measurements and monitoring, for example in pulsoximetry, but it is not limited thereto and may also be used for alternative applications.

SHORT DESCRIPTION OF THE FIGURES

The invention will be explained in more detail below with reference to the drawings, in which identical or functionally equivalent or similar items have been given the same reference symbols.

Figure 1B:
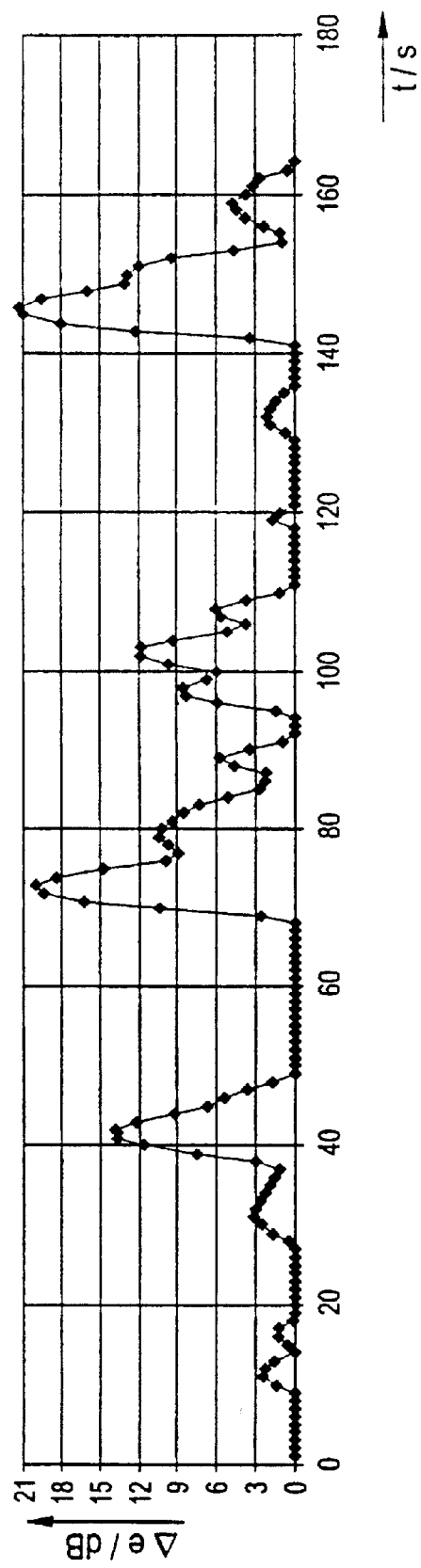
Figure 2:
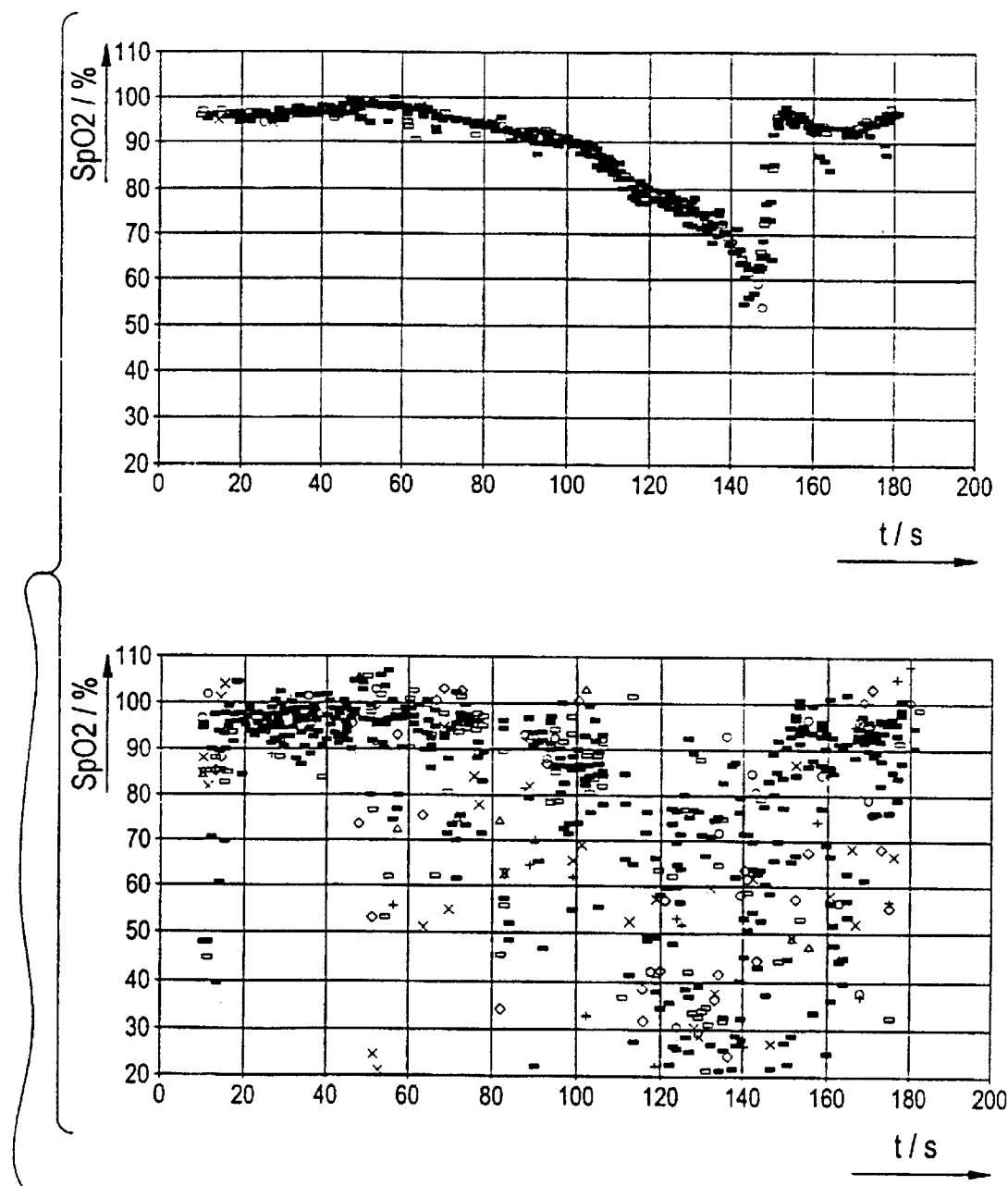
Figure 3A:
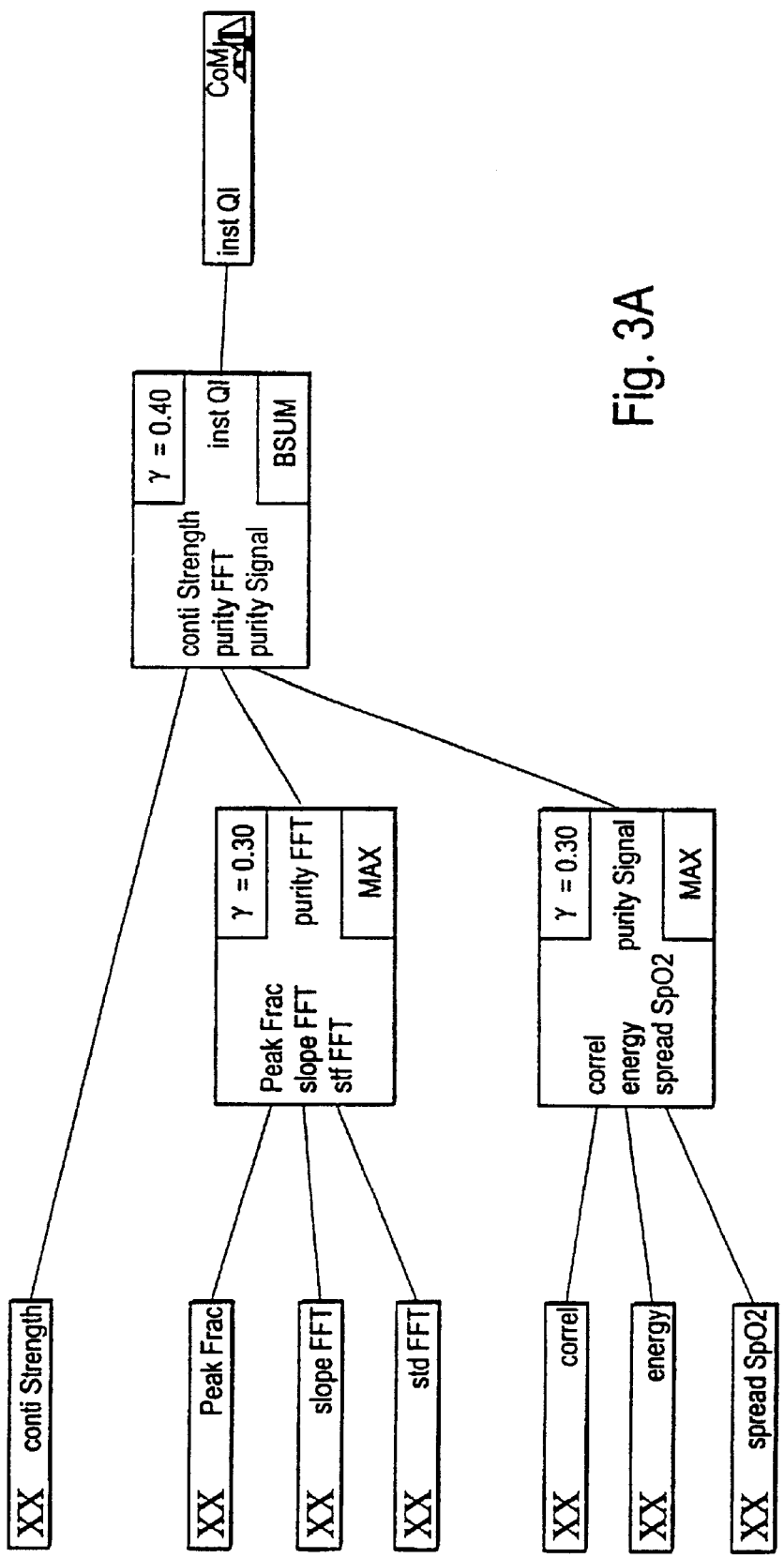
Figure 3B:
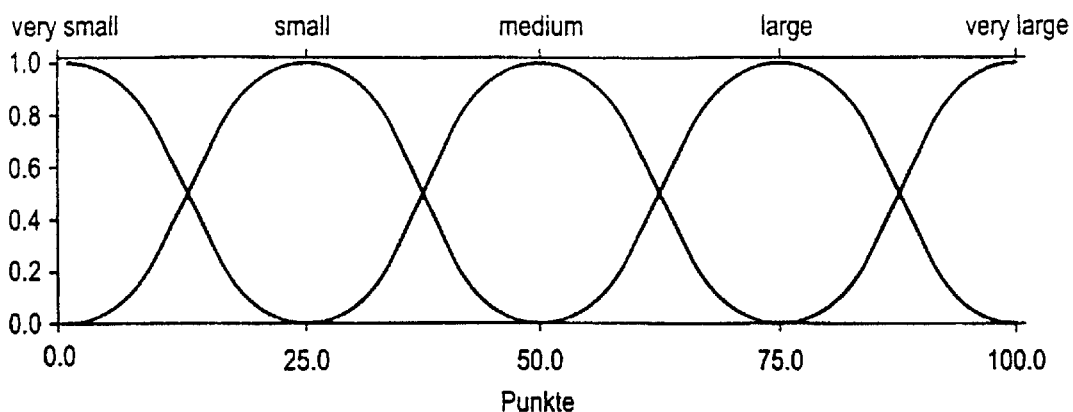
Figure 3C:
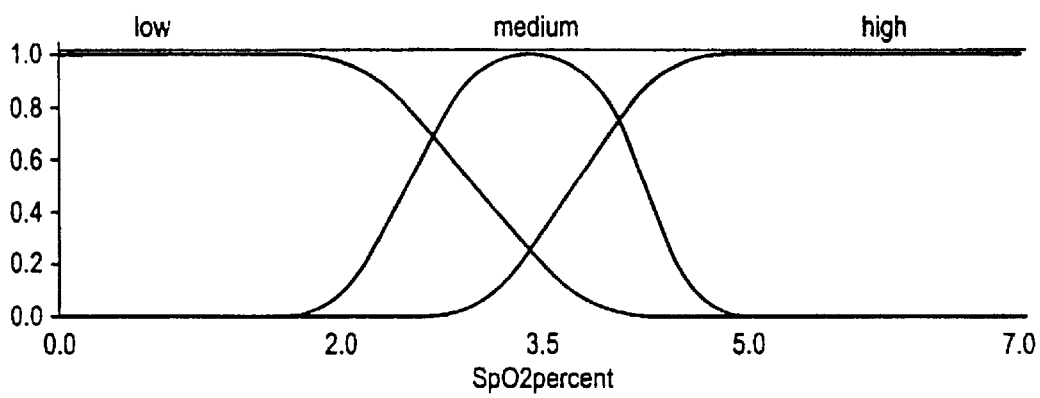
Figure 3D:
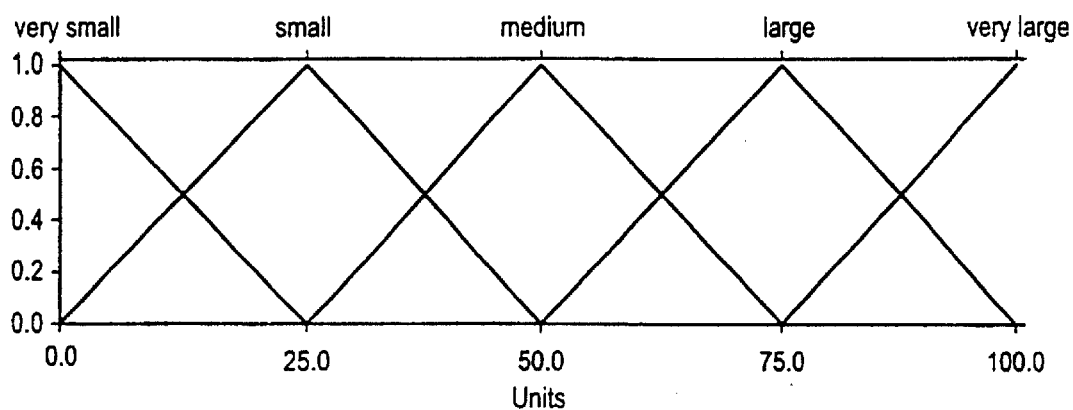
Figure 4D:
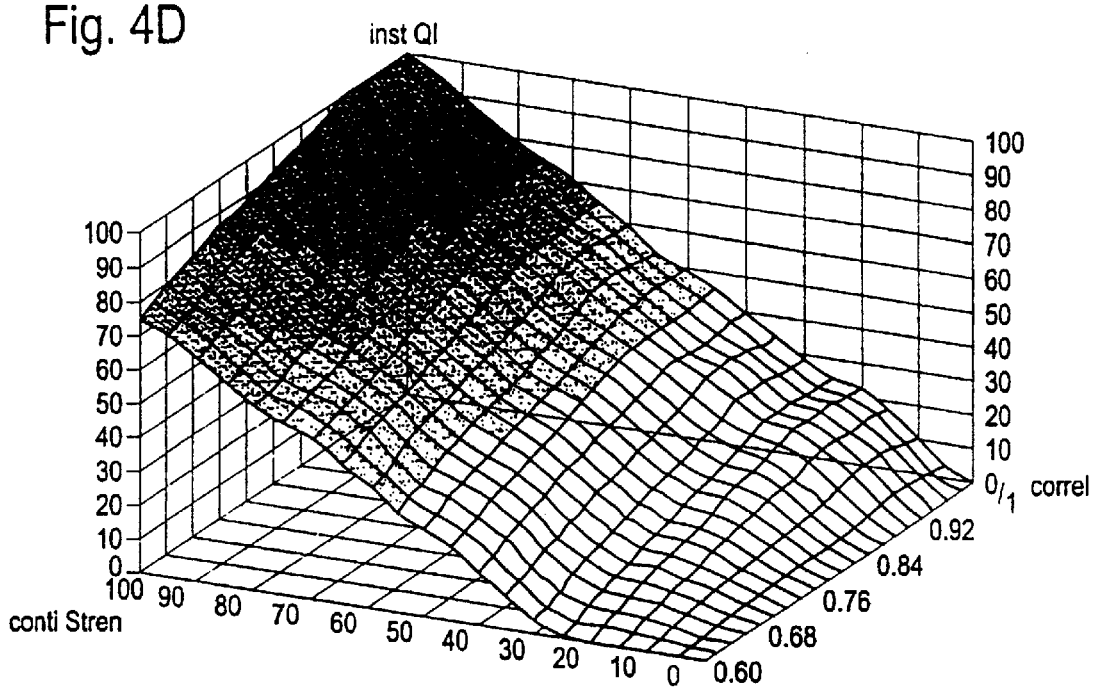
Figure 4E:
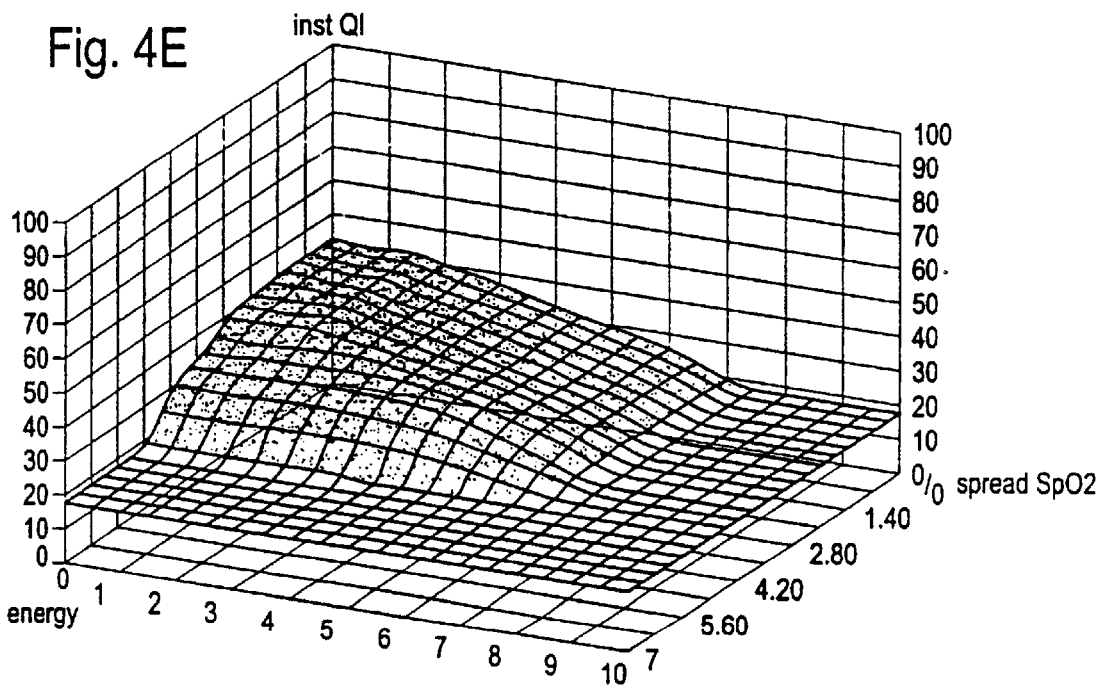
Figure 5:
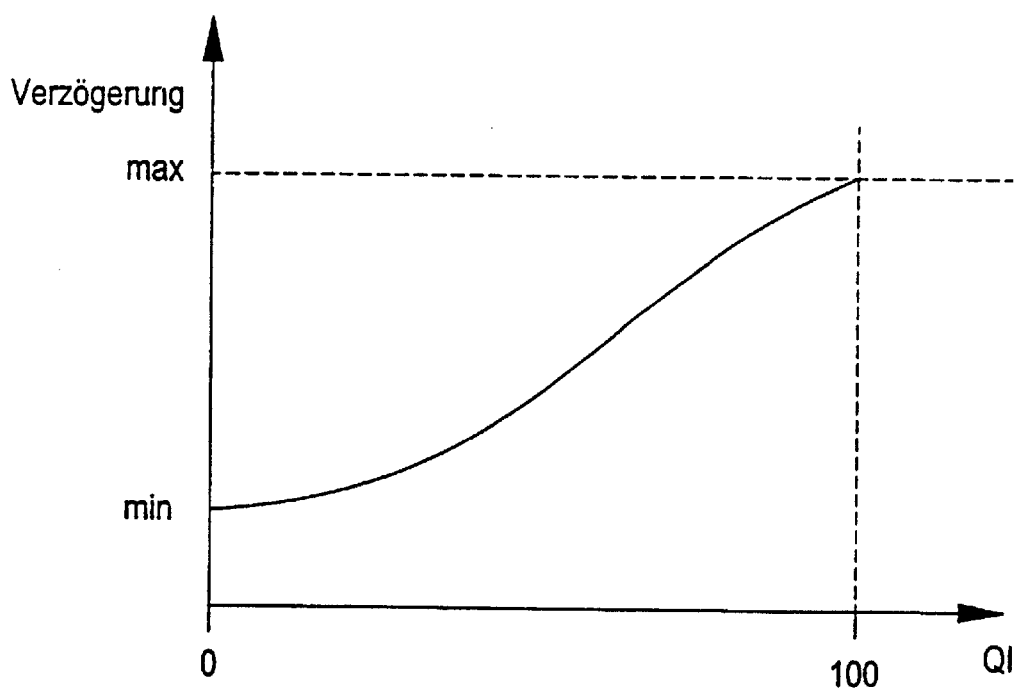

FIGS. 1A and 1B show the energy factor $\Delta e$ by way of example for an episode without and an episode with interference, FIG. 2 shows an example of the $SpO_2$ spread of the needles of the FNA, FIG. 3A is a block diagram of the 2-stage structure of the fuzzy link QI, FIGS. 3B and 3C are examples of possible graphic functional representations of the variables, FIG. 3D shows the member functions of the output variables "instQI", FIGS. 4A to 4C show control lines of the preliminary stages, FIG. 4D shows the control surface in dependence on the family strength "contiStrength" and the correlation of the time signals "correl", FIG. 4E shows the control surface in dependence on the energy fluctuation "energy" and the $SpO_2$ spread "spreadSpO2", and FIG. 5 shows an example of a gradient of the delay time plotted against the value of the quality indicator QI.

DETAILED DESCRIPTION OF THE DRAWINGS

A preferred embodiment for determining a quality indicator according to the invention will now be explained below for a pulsoximetric measurement as described in detail, for example, in EP-A-870466 (also referred to as "pin cushion algorithm") or in the international patent application (internal reference no. of applicant 20-99-0012 with the same date of application as the present application: also referred to as "fuzzy needle algorithm" or FNA), both from the same applicant and from the same inventor as the present invention. In as far as these disclosures are necessary for understanding the following embodiment, they are to be included herein by reference so as to form part of the present disclosure. The factors proposed for determining the quality indicator relate first and foremost to the pulsoximetry algorithm of the latter cited application which is based on the former cited application in that respect and forms a further development thereof.

The first cited application EP-A-870466 ("pin cushion algorithm") is based on a selection of the pulsoximetric signal in accordance with the physiological relevance of the frequency components. After an optional suppression of the DC component in both pulsoximetric basic signals (red and infrared), the basic signal values present in a progressing time window are transformed by Fourier transforms (Fast Fourier Transforms in this case, FFTs) into the frequency domain. Ratios of the coefficients of the amplitude spectrum are formed from the transformed basic signals for all frequency points. When the infrared spectrum is plotted on the x-axis and the red spectrum on the y-axis, a graph is obtained which shows needle-type peaks. These needles correspond to the peaks of the spectra, very thin needles being obtained for uninterfered signals, while the respective needles of the fundamental mode and the harmonics lie on top of one another. The angle of each needle with respect to the axis then corresponds to the saturation value. Since the representation of the spectra in this graph shows a similarity to a pin cushion, the method of EP-A-870466 is also referred to as "pin cushion algorithm".

To identify the needle representing the pulsoximetric signal, first one of the complex amplitudes of the red and infrared spectra is determined in the pin cushion algorithm. The distance spectrum describes the distance of each single support point in the needle diagram to the origin. The individual needles are determined from this distance spectrum through consideration of the maxima and the base points connected thereto. Only those needles which fulfill a series of given criteria are retained for further consideration. The selection of needles thus reduced is subjected to a further classification. Needles representing the useful signal must fulfill the following criteria: the peaks must fit well into a harmonic frequency series, as many harmonic waves as possible should be present, the needles should be as thin as possible, and the frequency of the fundamental wave as well as the saturation value, the perfusion, and the pulse rate must lie within the physiological ranges. Then an overall evaluation takes place for each needle through the assignment of a number of points or a K.O. criterion for each of these criteria. The needle which receives most points, in other words which fulfills the criteria best, and which has at least a minimum number of points, is retained for determining the output value for the pulsoximetric measurement value. Optionally, a comparison with preceding output values may be carried out as a plausibility check, and the newly determined output value will be rejected in the case of a significant deviation from the preceding output values, in which case no new value will be displayed.

In the international patent application cited last (FNA—internal reference of applicant 20-99-0012) a periodic useful signal in a measurement signal (with noise) is recognized in a multistage process, as follows.

In a first step, a transform (for example, FFT) is carried out for a given time window of the measurement signal in the frequency range. Optionally, the measurement signal may be filtered before or after the transform. Preferably, such a filtering takes place, for example, through a reduction in the DC component (in particular as described in EP-A-870466 or EP-A-870465) and/or through suppression of transient interferences (in particular as described in applicant's international patent application with the same date of application and internal reference 20-99-0010).

In a second step, an identification of frequency peaks (also referred to as needles) takes place in the transformed time window of the measurement signal with the aid of a distance spectrum as mentioned above.

In a third step, an assignment takes place according to which identified frequency peaks of the instantaneous time window are assigned to time gradients (also referred to threads) of identified frequency peaks of one or several preceding time windows, in as far as identified frequency peaks are present already. This "concatenation of the needles into threads" takes place by means of an initialization, for example in the case of a restart, in which the first obtained set of needles is taken for founding a set of threads. A progressing series of fitting needles joins itself thereto, a needle being regarded as fitting if few deviations from given criteria are present in comparison with the last member in the thread. The decision as to whether a needle is regarded as fitting is made by means of a linkage of given criteria through fuzzy logic. If no new needle can be assigned to a thread which is present, a void will remain, and the thread will either be ended or be replaced by a new thread.

In a fourth step, an assignment of the time gradients (threads) to one or several families is made, each family consisting of a fundamental wave and one or several harmonics. Such an assignment or concatenation of the threads into harmonics takes place through an investigation as to the extent to which certain characteristic features are shared by the threads, which together will form an indication that the threads belong to the same useful signal. Such an investigation takes place through linkage of suitable criteria such as harmonic frequency relation, expected amplitude drop of the harmonics range, and/or a development of similar relative trends of the frequencies and/or amplitudes. Linking of the criteria takes place again through fuzzy logic.

In a fifth step, a selection of a family then takes place as that family which is to represent the useful signal, which selection should be seen in the light of a highest probability. The selection of a family takes place through the interlinking of given criteria such as the existence of a fundamental mode, a first harmonic, and a second harmonic, average accuracy of fit of the threads, number of valid needles in a thread (i.e. the length of the thread), consistency or "porosity" of a thread, and the quality of the relation between the fundamental and the first harmonic, between the fundamental and the second harmonic, and between the first harmonic and the second harmonic. The linking of the criteria again takes place through fuzzy logic. The selection of a family may alternatively or additionally take place through a plausibility test of the family in comparison with preceding output values, such that the most plausible family is selected.

In a sixth step, finally, a frequency peak (a needle) of the instantaneous time window is chosen from the selected family as that one which is to represent the measurement value of the useful signal in this time window, the selection being on the ground of highest probability again in this case. The instantaneous measurement value of the useful signal may then be calculated or otherwise determined from this chosen frequency peak, in as far as this peak does not already represent the measurement value itself. The selection of the frequency peak representing the instantaneous measurement value of the useful signal takes place in that a link is established between given criteria by means of fuzy logic. Criteria used for this are those criteria which were adjusted with regard to achieving a plausibility of the instantaneous measurement value in relation to preceding measurement values and/or in relation to expected or meaningful values.

After the frequency peak has been selected in the sixth step, a plausibility test may be carried out so as to check whether the selected frequency peak actually corresponds to an expected measurement value of the useful signal and whether a measurement value derived from the selected frequency peak is to be given as an output, or whether no measurement value at all is to be given out for this time window. Such a plausibility test takes place by means of a comparison of the instantaneous measurement value with preceding measurement values and/or with expected or meaningful values.

Whereas in the pin cushion algorithm described in EP-A-870466 the values from the past are taken into account only for selecting a needle from the fundamental mode to be put out, the values from the past are taken into account for selecting a harmonic family of threads, comprising both the fundamental and the harmonic wave(s), in the international patent application (FNA) cited last. A family member is then selected from the selected harmonic family, which member is to represent the instantaneous measurement value of the useful signal.

In the embodiment of the present invention, a series of input factors are used for controlling the quality indicator, each factor individually and in combination with the others having a relevant relationship to the quality of the signal and to the quality of the calculated output values. The factors may be defined on the one hand by elements which can be continuously determined from the basic signals and which are independent of the actual pulsoximetry algorithm. On the other hand, elements may be included here which derive directly from the pin cushion algorithm or the FNA and which are attuned to the performance thereof. The interlinking of the elements into a summed quality factor is preferably achieved by means of a fuzzy operation.

Various input factors suitable for controlling the quality indicator will be discussed below. As many factors as possible are preferably combined so as to enhance the reliability of the quality indicator. The number thereof, however, may be limited and determined in particular by the performance of a computer system calculating the quality factor and by the respective pulsoximetry algorithm used.

A. Basic Signal Factors

Factor 1: Correlation of the Basic Signals Red and IR

The correlation of the basic signals (in the time domain) between red and infrared (IR) must have a certain minimum value, otherwise the further processing of the signal will be blocked in that no more needles are derived. Furthermore, this correlation is also taken into account in the choice of a so-called "inop text" for characterizing inoperative states: if the correlation is too small, a message appears as an "inop text" such as, for example, "noisy signal".

If the signal is not noisy, it is clear that the red and IR signals must result in two fully synchronous plethysmograms, which thus will lead to an ideal correlation factor r=1. A degradation of the correlation factor r points to superimposed, decorrelated interferences, such as those which may occur in the case of noise, ambient light, electromagnetic interference (from high-frequency surgery, interfering radiation from other medical appliances, cellular telephones, etc.).

Factor 2: Energy Fluctuations

In the case of a noise signal without noise, the energy (defined as the sum of all squared scanned values of the time window) present within an FFT window (for example of 8 s) varies little over time. It is only the physiological circulation control mechanisms and position changes of the patient which provide a certain variability. Movement interferences lead to massive, often eruptive changes in the trend, in contrast to the moderate natural energy fluctuations.

To calculate the fluctuation width, energy values e(t) are preferably determined in a rhythm of once every second of the algorithm. The AC signals of the two channels red and IR present in the window are used for this, with $e(t)=e_{red}+e_{IR}$, with $e_{red}$ being the energy value of the red channel and $e_{IR}$ the energy of the IR channel.

A moving trend is formed from the energy values e(t) every second, preferably reaching back over 20 s into the past. A sudden upward leap of the energy is regarded as an indicator for interference. A sudden drop is not considered. A rank function $rank_\alpha$ is used as a measure for the base level. A rank function determines that value from a random sample which is in a certain ranking position in the ordered random sample, analogous to a median filter which results in the average value of the ordered series. A parameter a (with values between 0 and 1) indicates the rank. A value $\alpha=0$ corresponds to the minimum function, $\alpha=0.5$ the median function, and $\alpha=1$ the maximum function.

A rank parameter $\alpha=0.2$ was found to be suitable for the purposes of the invention. It achieves that an energy value between the minimum and the average value (median) is taken as a reference value. It is useful to take this close to the minimum because continuous strong energy bursts will not incorrectly pull the reference value in upward direction as a result. It is not advisable to go entirely to the minimum because there may also be moments when the useful signal and the noise are partly extinguished and lead to an energy collapse which would not be the correct baseline reference point.

The energy fluctuation factor for calculating the quality indicator is preferably determined in accordance with the equation:

$$\Delta e = \max(e(t) - rank_{\alpha=0.2}(e(t)), 0)$$

$$t = \{-20s, -19s, \ldots, 0s\}$$

The maximum function limits the smallest possible value to 0 because collapses will not be taken into account. Preferably, the logarithmic measure (dB) for the energy e is used so as to keep control over the wide dynamics in the case of major interferences. FIG. 1 shows the energy factor $\Delta e$ by way of example for an episode without noise (FIG. 1A) and with noise (FIG. 1B). Fluctuations of up to approximately +5 dB are to be considered normal; artifacts are to be presumed over and above that value.

Factor 3: Decline of the Spectrum

A further measure for the quality is the "purity" of the spectrum. A pulse signal always shows a typical pattern of its amplitude spectra: a dominant fundamental wave with more or less steeply dropping harmonics. According to the invention, a connecting line is drawn through all spectral coefficients A. If the slope m thereof is standardized to an average value $\overline{A}_i$ of the spectral coefficients, an amplitude-independent measure $m_n$ is obtained for the decline in accordance with $m_n = m/\overline{A}_i$, with m being the slope of the regression line.

In the case of good signals, the spectrum declines regularly by more than approximately −20%/Hz. Values of above −10%/Hz, i.e. a weak drop or even a rise, can be observed in the case of marked interferences only, especially when they have a higher frequency.

Factor 4: Variability of the Spectral Coefficients

Besides the decline of the spectrum, the variability of the coefficients within the spectrum also constitutes a measure for the "purity". An unquiet gradient with many peaks points to interferences. A degree of spread a around the connecting line can be determined within the framework of the calculation of the connecting line or regression line. If the degree of spread σ (as indicated above) is standardized to the average value $\overline{A}_i$, an amplitude-independent spread factor $\sigma_n$ with $\sigma_n = \sigma/\overline{A}_i$ is obtained, in which σ is the spread value around the connecting line (the so-called empirical residual variance).

The spread factor $\sigma_n$ lies in a range of 2 to 3 in the case of good signals; i.e. a strong spread is present. The predominant number of the spectral coefficients lies either clearly above the connecting line (peaks) or clearly below it (background, close to 0). Values of the spread factor $\sigma_n$ below 2 point to a strong fluctuation in the spectrum; the background between the harmonics of the pulse wave is filled with noise.

B. Algorithm-Related Factors

Whereas the above criteria for the quality were formed either from the time signal or from the Fourier-transformed signal, three more factors will now be discussed which are applied to interfaces in the actual FNA. They accordingly characterize substantially those properties which are important for a correct functioning of this algorithm. If an algorithm other than the FNA is used, other quality-relevant characteristics are to be obtained for this algorithm.

Factor 5: Proportion of the Peak Surfaces in the Spectrum

This factor is determined far forward in the algorithm. It relates to a determination of the sum of the surface areas of all detected peaks in the spectrum in relation to the total surface area covered by the spectrum. Experiments have shown that this quantity forms a useful supplement to the preceding factor (variability of the spectral coefficients) in many situations. Values above 20% are to be regarded as good, while below approximately 5% the background noise is highly dominant.

Factor 6: Width of the $SpO_2$ Spread of All Needles

Each needle is given a $SpO_2$ value in the characterization of all peaks. In signals with little noise, the harmonics of the pulse are the only peaks present. Their $SpO_2$ values differ only slightly; the difference lies in the order of magnitude of 1%. Interferences usually introduce new components in the form of needles, or they are superimposed on the peaks and falsify the $SpO_2$ values thereof. Each false needle, i.e. not belonging to the useful signal, represents a potential risk because it could possibly enter a thread and thus give an erroneous contribution if this thread were to be given as an output.

FIG. 2 shows an example of the $SpO_2$ spread of the needles, with the upper graph showing an undisturbed basic episode, i.e. a volunteer holding his breath. The lower graph shows a strongly noise-interfered episode, the same episode as shown in FIG. 2 above, but with noise superimposed, so that the needles partly deviate strongly from the required values. The strongly deviating needles, however, are also often weak and are of limited importance in weighting of the degree of spread. The width of spread thus rises within the needles of an FNA cycle.

A further gradual measure is thus available with a weighted spread $\sigma_{SpO2}$ for providing a statement on the signal quality. If this parameter is considered for noise-free basic episodes and for noise-laden episodes, the following mirrored boundary values in the fuzzy logic assignment functions are obtained: up to 1.5%, the valuation is to be regarded as "good", from 4.5% upwards it is to be regarded as "bad".

Factor 7: Strength of the Output Thread Family

A decisive factor in FNA is the strength of the output family, which factor is also proportionally the strongest in the fuzzy operations (explained below) for linking together all quality-relevant parameters. Many characteristics have already been joined together therein in the preceding algorithm steps. As the word "strength" indicates, the value says something about the quality of the output values. The strength (contiStrength) preferably lies in a range from 0 to 100 points and represents the qualitative properties of algorithm-relevant factors.

C. Combination of the Factors

Each of the seven factors described above is the bearer of a quantity of information as to the quality of the processed signals, and accordingly as to the reliability of the pulsoximeter output values. In a fuzzy operation QI (explained in more detail below), these factors are joined together into an output message. A multistage fuzy operation is preferably used in view of the high number of parameters so as to obtain a score for the quality, preferably lying in a range of 0 to 100 points, as the final result.

A quality indicator (QI) value (instQI) is obtained as the result of the fuzzy operation in each cycle. This value may fluctuate considerably from one cycle to the next in the case of signals with a strong noise component. To achieve that the display acts somewhat more quietly, a slight low-pass filtering is preferably carried out in the form of a simple infinite impulse response (IIR) filter: $QI_n = 0.8 QI_{n-1} + 0.2 instQI_n$.

The Fuzzy Operation

The interlinking of the (at most) seven factors described above, which may be used for defining the quality indicator QI, will now be explained for a preferred embodiment. The identifiers used here correspond to the symbols used above, as follows:

| | |
|---|---|
| correl = | factor 1: r, correlation of the time signals read with infrared |
| energy = | factor 2: $\Delta e$, energy bursts in dB |
| slopeFFT = | factor 3: $m_n$, decline of the (distance) spectrum in % /Hz |
| stdFFT = | factor 4: variability of the spectral coefficients |
| PeakFrac = | factor 5: proportion of the surface area of the peaks in relation to the total surface area of the spectrum in % |
| spreadSpO2 = | factor 6: (weighted) $SpO_2$ spread width of all needles in one cycle in % $SpO_2$ |
| PStrength = | factor 7: family strength of the output family expressed in points |
| instQI = | resulting value of this fuzzy operation expressed in points: non-averaged quality indicator. |

The most important parameters of this fuzzy operation will be described below. A two-stage fuzzy structure with two purely linguistic intermediate variables was chosen. The complexity of the lines remains manageable as a result of this. In a single-stage variant, seven input quantities with three assignment functions each would lead to a complete set of rules of $3^7 = 2187$ rules. FIG. 3A gives an overview of the two-stage structure of the fuzzy interlinking QI with the seven input quantities and three blocks of rules. A total overview of this fuzzy operation QI shows seven linguistic input variables, one linguistic output variable, two linguistic intermediate variables, three blocks of rules, 62 rules, and 34 assignment functions. The linguistic variables used for the fuzy operation are:

| Variable Name: | Type: | Classification Names: |
|---|---|---|
| contiStrength | input | very_small, small, medium, large, very large |
| correl | input | low, medium, high |
| energy | input | low, medium, high |
| PeakFrac | input | bad, medium |
| slopeFFT | input | steep, medium, flat |
| spreadSpO2 | input | low, medium, high |
| stdFFT | input | bad, medium, good |
| purityFFT | intermediate | low, medium, high |
| puritySignal | intermediate | low, medium, high |
| instQI | output | very_low, low, medium, high, very high |

As an example of a possible graphic functional representation of the variables, FIG. 3B shows an example relating to the variable "contiStrength", and FIG. 3C an example relating to the variable "spreadSpO$_2$". The gradients of the other variables may be represented in a similar manner. The properties of the input variables may be represented as follows:

| Output Variable | Min | Max | Unit |
|---|---|---|---|
| contiStrength | 0 | 100 | points |
| correl | 0.6 | 1 | |
| energy | 0 | 10 | dB |
| PeakFrac | 0 | 40 | % |
| slopeFFT | −25 | −10 | % /Hz |
| spreadSpO$_2$ | 0 | 7 | SpO2 % |
| stdFFT | 0.5 | 3 | |

Defuzzification was carried out by the center-of-maximum (CoM) method (cf. Altrock C.; "Fuzzy Logic: Band 1, Technologie" (Fuzzy Logic: Part 1, Technology), Oldenburg Verlag, Munich, 1995), so as to achieve a compromise between simultaneously applicable rules. FIG. 3D shows the member functions of the output variable "instQI" with the following properties:

| Output variable | Min | Max | Unit | Defuzzification |
|---|---|---|---|---|
| instQI | 0 | 100 | points | CoM |

The even subdivision of the five functions (cf. FIG. 3D) provides a comparatively "linear" picture of the rules in accordance with the CoM method.

The Rules

1. The preliminary stage "purityFFT": the three inputs relating to the spectral properties of the signal are jointly evaluated here and interlinked into a kind of "purity factor"

of the spectrum. The table below shows the input and output interface of the block of rules "purityFFT":

| operator: | GAMMA |
|---|---|
| parameter: | 0.30 |
| result operator: | MAX |
| number of inputs: | 3 |
| number of outputs: | 1 |
| number of rules: | 13 |

FIG. 4A shows the control basis of the preliminary stage "spectral purity" (purityFFT). The bad characteristic of one parameter is sufficient for degrading the result.

2. The preliminary stage "puritySignal": three further inputs also relating to the "purity" of the signal, i.e. the correlation, the energy constancy, and the $SpO_2$ spread of all needles, are combined here. The table below shows the input and output interface of the control block "puritySignal":

| operator: | GAMMA |
|---|---|
| parameter: | 0.30 |
| result operator: | MAX |
| number of inputs: | 3 |
| number of outputs: | 1 |
| number of rules: | 12 |

FIG. 4B shows the control basis of the preliminary stage "purity of the signal" (puritySignal). The bad characteristic of a single parameter is sufficient for degrading the result (cf. "don't care" fields).

3. The end stage: the intermediate results and the family strength (contiStrength) not yet considered are combined here. The latter is explicitly strongly weighted in the management of the 37 rules. The table below shows the input and output interface of the block of rules "instQI":

| operator: | GAMMA |
|---|---|
| parameter: | 0.40 |
| result operator: | BSUM |
| number of inputs: | 3 |
| number of outputs: | 1 |
| number of rules: | 37 |

FIG. 4C shows the control basis of the preliminary stage "instQI". Only good pairs will lead to a very good quality indicator.

FIG. 4D shows the control surface in dependence on the family strength "contiStrength" and the correlation of the time signals "correl". All other parameters were set for their optimum values. The influence of the correlation is indeed clearly observable, but nevertheless quite weak when compared with the family strength.

FIG. 4E shows the control surface in dependence on the energy fluctuation "energy" and the $SpO_2$ spread "spread-SpO2". All other parameters were set for their optimum values, with the exception of a moderate family strength "contiStrength"=42 points. Starting from a certain point, a positive, but moderate influence on the quality indicator QI exerted by the two above parameters is observable.

The manner of operation of this fuzzy logic mechanism can only be suggested by means of the diagrams of FIGS. 4D and 4E, because very many control surfaces will result from the many inputs. Since the family strength largely represents the criterion for the FNA, it was given a high importance and a corresponding weight.

D. Alarm Triggering and Trend Derivation

In a preferred further embodiment, a delay time for switching-on of an alarm, after an alarm condition has been triggered, is set for a maximum in the case of a low value of the quality indicator (low reliability), and thus a very low signal quality, because in this case the probability of possible false alarms is at its highest. At a high quality indicator value (high reliability), by contrast, the risk of a false alarm is low, and the alarm delay time is set for a lower value. The delay time may be automatically and continuously adapted between a minimum and a maximum delay value in dependence on the value of the quality indicator.

FIG. 5 shows an example of a gradient of the delay time plotted against the value of the quality indicator QI, wherein the gradient is flattened out towards the extreme values of the delay time. Alternatively, however, the gradient may be adapted to the respective circumstances so as to be linear or to have some other shape. Preferably, the minimum and the maximum delay time can be configured by the user, and/or the gradient of the delay time as a function of the quality indicator may be adjustable, for example through the selection of given gradients.

In a further embodiment, the quality indicator value is represented together with the $SpO_2$ value and the pulse rate as a trend and simultaneously recorded. As a result of this, $SpO_2$ and pulse rate results can be qualified as artifacts or genuine events in a retrospective trend observation. Furthermore, a prognosis as to measuring problems to be expected is possible by means of the gradient of the quality indicator trend. Thus a deterioration in the perfusion or an increase in the movements (for example shivering with cold in the wake-up room) can be recognized earlier. The clinical personnel can accordingly already react thereto before a (false) alarm is generated.

What is claimed is:

1. A method of determining a quantitative statement concerning the quality of a medical measurement signal in pulsoximetry, said method comprising the steps of:
   (a) determining factors relevant to the measurement signal, the factors relating to combinations selected from the group consisting of signal recording, signal processing, and signal evaluation; and
   (b) interlinking the factors by means of an uncertain logic, including fuzzy logic, into a quality indicator wherein the quality indicator quantitatively describes a quality of a determined measurement value of the measurement signal.

2. The method as claimed in claim 1, wherein the step of determining factors relevant to the measurement signal comprises:
   a step of determining factors relative to an obtaining of the measurement signal, wherein the factors describe at least one of a measurement location, a measurement time, and a measurement sensor arrangements;
   a step of determining factors relevant to signal processing, wherein the factors describe at least one of a signal-to-noise ratio, parameters relating to a possible subsequent noise suppression, and a signal compression; and
   a step of determining factors relevant to the signal evaluation, wherein the factors describe at least one of measuring algorithms used, and consideration of at least one of all basic signals and parts of all basic signals thereof.

3. The method as claimed in claim 1, further comprising:
   providing a display of the quality indicator by means of a tendency display having a nature selected from at least one of "relatively better/worse" and "absolutely good/bad", the tendency display further including a display with histogram bars of variable length.

4. The method as claimed in claim 1, wherein a visualization of the quality indicator is achieved using a display of the measurement signal describing the quality indicator that changes when the quality indicator value exceeds a given threshold value, wherein the visualization includes at least one selected from the group consisting of a switch-over from a continuous display to a flashing display with a varying flashing frequency in dependence on the quality indicator value, a change in display color including at least one of: a) red for low quality indicator values b) green for a high quality indicator value, amber for a medium quality indicator value, and red for a low quality indicator value and c) an inversion of display colors.

5. The method as claimed in claim 1, further comprising:
controlling an alarm function in dependence on the quality indicator in response to the measurement signal deviating from at least one of a given limit value and a range.

6. The method as claimed in claim 5, wherein controlling the alarm function includes a change in an alarm delay time in dependence on a value of the quality indicator, wherein the alarm delay time is set for at least one of a maximum in the case of a low reliability of the measurement signal and a minimum in the case of a high reliability of the measurement signal.

7. The method as claimed in claim 1, further comprising a step of:
evaluating a gradient in time of the quality indicator so as to recognize at least one trend in the measurement signal.

8. The method as claimed in claim 7, wherein the trend is shown on a trend display, the trend display including an arrow pointing upwards for an improvement in signal quality, an arrow pointing downwards for a deterioration of signal quality, and an arrow remaining at a same level for indicating a substantially constant signal quality.

9. The method as claimed in claim 7, further comprising performing an error prognosis step based on the trend in the measurement signal and by giving an alarm in response to a substantially continuous drop in the quality indicator value over a given time period.

10. A computer program including a computer program product stored on a computer-readable storage medium, the computer program comprising a code for carrying out the steps as claimed in claim 1, wherein the program is carried out on a computer.

11. A device for determining a quantitative statement as to the quality of a medical measurement signal in pulsoximetry, the device comprising:
means for determining factors relevant to the measurement signal, the factors relating to a combination selected from the group consisting of signal recording, signal processing, and signal evaluation, and
means for interlinking the determined factors by means of an uncertain logic, the uncertain logic including fuzzy logic, to form to provide a quality indicator that quantitatively describes a quality of a determined measurement value of the measurement signal.

12. An apparatus for determining an oxygen content of blood by pulsoximetry, the apparatus comprising a device for determining a quantitative statement concerning the quality of a measurement signal as claimed in claim 11.

* * * * *